(12) United States Patent
Aman et al.

(10) Patent No.: US 10,993,729 B1
(45) Date of Patent: May 4, 2021

(54) STERILE READY-TO-USE SURGICAL TOOL AND ATTACHMENT SYSTEM

(71) Applicants: Peter M Aman, Austin, TX (US); Richard Acevedo, Austin, TX (US)

(72) Inventors: Peter M Aman, Austin, TX (US); Richard Acevedo, Austin, TX (US)

(73) Assignee: INSURGICAL, INC., Austin, TX (US)

( * ) Notice: Subject to any disclaimer, the term of this patent is extended or adjusted under 35 U.S.C. 154(b) by 34 days.

(21) Appl. No.: 16/143,450

(22) Filed: Sep. 26, 2018

Related U.S. Application Data (63) Continuation-in-part of application No. 14/746,841, filed on Jun. 23, 2015, now abandoned.

(60) Provisional application No. 62/020,387, filed on Jul. 2, 2014.

(51) Int. Cl.
| | |
|---|---|
| *A61B 17/16* | (2006.01) |
| *A61B 17/14* | (2006.01) |
| *B25F 3/00* | (2006.01) |
| *A61B 17/00* | (2006.01) |

(52) U.S. Cl.
CPC ........ *A61B 17/162* (2013.01); *A61B 17/1622* (2013.01); *A61B 17/1628* (2013.01); *A61B 2017/0023* (2013.01); *A61B 2017/0042* (2013.01); *A61B 2017/00398* (2013.01); *A61B 2017/00477* (2013.01); *A61B 2017/00734* (2013.01); *B25F 3/00* (2013.01)

(58) Field of Classification Search
CPC .............. A61B 17/162; A61B 17/1622; A61B 17/1628; A61B 2017/0023; A61B 2017/00398; A61B 2017/0042; A61B 2017/00477; A61B 2017/00734; B25F 3/00

See application file for complete search history.

(56) References Cited

U.S. PATENT DOCUMENTS

| | | | | |
|---|---|---|---|---|
| 2,541,306 A | * | 2/1951 | Taylor | B23B 49/02 408/111 |
| 3,540,322 A | * | 11/1970 | Swanson | B23B 49/02 408/112 |
| 3,910,589 A | | 10/1975 | Derbyshire | |
| 3,975,032 A | * | 8/1976 | Bent | B23B 31/22 279/30 |
| 4,091,880 A | * | 5/1978 | Troutner | A61B 17/1628 173/170 |
| 4,653,358 A | * | 3/1987 | Lankry | B25B 21/007 81/429 |
| 4,736,742 A | * | 4/1988 | Alexson | B27B 19/006 606/80 |

(Continued)

FOREIGN PATENT DOCUMENTS

| | | |
|---|---|---|
| DE | 3443186 A1 | 5/1986 |
| DE | 19622486 C1 | 10/1997 |

(Continued)

*Primary Examiner* — Nathaniel C Chukwurah
*Assistant Examiner* — Lucas E. A. Palmer
(74) *Attorney, Agent, or Firm* — Clearpat Services, LLC; Brian Burkinshaw (57) ABSTRACT

A surgical tool and attachment system includes a surgical power tool including a housing and rotary powered driver. A power tool accessory unit includes a power tool accessory driver and an attachment member connected to the housing. A coupling interconnects the rotary powered driver and the power tool accessory unit.

21 Claims, 7 Drawing Sheets

(56) References Cited

U.S. PATENT DOCUMENTS

| | | | | |
|---|---|---|---|---|
| 4,806,730 | A | * | 2/1989 | Alexson .............. A61B 17/1624 216/65 |
| 4,834,092 | A | * | 5/1989 | Alexson .............. A61B 17/1624 279/24 |
| 5,207,127 | A | * | 5/1993 | Nick ........................ B25B 23/10 81/429 |
| 5,387,217 | A | | 2/1995 | Sefcik |
| 5,794,715 | A | * | 8/1998 | Norman ............... A61B 17/162 173/104 |
| 5,839,897 | A | | 11/1998 | Bordes |
| 5,902,306 | A | * | 5/1999 | Norman .............. A61B 17/1697 606/104 |
| 5,993,454 | A | * | 11/1999 | Longo ................ A61B 17/1624 606/80 |
| 6,033,409 | A | * | 3/2000 | Allotta ............... A61B 17/1622 606/170 |
| 6,095,530 | A | | 8/2000 | Rohm |
| 6,129,363 | A | | 10/2000 | Mack |
| 6,494,892 | B1 | | 12/2002 | Ireland |
| 7,115,119 | B2 | | 10/2006 | Desarzens |
| 8,419,760 | B2 | * | 4/2013 | Wiebe, III ......... A61B 17/1628 279/145 |
| 2003/0230423 | A1 | | 12/2003 | Izumisawa |
| 2004/0010250 | A1 | * | 1/2004 | Manna ........... A61B 17/320068 606/42 |
| 2006/0259055 | A1 | * | 11/2006 | Thorne .............. A61B 17/1622 606/180 |
| 2008/0027449 | A1 | | 1/2008 | Gundlapalli |
| 2009/0264940 | A1 | * | 10/2009 | Beale .................. A61B 5/04001 606/86 R |
| 2010/0047737 | A1 | * | 2/2010 | Richard .................. A61C 1/082 433/75 |
| 2010/0152739 | A1 | | 6/2010 | Sidebotham |
| 2010/0262127 | A1 | * | 10/2010 | Schmied ........... A61B 17/1624 606/1 |
| 2010/0311006 | A1 | * | 12/2010 | Lancieux ............. A61C 8/0089 433/75 |
| 2011/0264074 | A1 | * | 10/2011 | Tegg ........................ A61B 8/12 604/523 |
| 2013/0204254 | A1 | | 8/2013 | Slone |
| 2013/0245629 | A1 | * | 9/2013 | Xie ...................... A61B 17/162 606/80 |
| 2013/0303330 | A1 | * | 11/2013 | Stevens .......... A61M 25/09041 475/349 |
| 2013/0307529 | A1 | | 11/2013 | Baumgartner |
| 2014/0276890 | A1 | * | 9/2014 | Khosla ................ A61B 17/162 606/103 |
| 2015/0005776 | A1 | * | 1/2015 | Biegun ............. A61B 17/1659 606/85 |
| 2015/0230823 | A1 | * | 8/2015 | Morgan ............. A61B 17/3476 604/272 |
| 2015/0351820 | A1 | * | 12/2015 | Straslicka .......... A61B 17/8897 606/169 |

FOREIGN PATENT DOCUMENTS

| | | |
|---|---|---|
| EP | 2387960 A2 | 11/2011 |
| EP | 2957245 A1 | 12/2015 |
| FR | 2924012 A1 | 5/2009 |
| GB | 82173729 B | 12/1988 |

\* cited by examiner

STERILE READY-TO-USE SURGICAL TOOL
AND ATTACHMENT SYSTEM

CROSS REFERENCE TO RELATED
APPLICATIONS

This application is a Continuation-in-Part of Non-Provisional application Ser. No. 14/746,841 filed Jun. 23, 2015, which is related to and claims priority to U.S. Provisional Application No. 62/020,387, filed on Jul. 2, 2014, which is incorporated by reference herein in its' entirety.

BACKGROUND

This disclosure relates to single and limited use surgical power tools and more specifically such tools which can be provided as a pre-packaged, pre-sterilized tool including a pre-installed charged battery. Such power tools usually include a power portion, a handle portion and a battery portion.

Important factors for any surgical instrument include sterility, cost of acquisition, maintenance, and reliability during use in the surgical suite. Each of these factors can have a significant impact on the cost of medical care for both the patient and the provider.

In recent years, there has been significant focus on the ever increasing cost of medical care. These cost increases have led to skyrocketing insurance premiums, reduced coverage, reduced reimbursements, increased fees for services, severe reductions in services for some patient groups by some providers, and unfortunately an apparent increase in infections and medical mishaps.

In an effort to reduce costs and improve profitability, both service providers and medical device suppliers are continuously looking for ways to streamline procedures, cut time, cost, and risk from their products and services without reducing the quality of the products or services they provide to their customers. One area to benefit from these savings and improvements has been in the orthopedic surgical field through the use of high precision, battery powered surgical instrumentation. In the late 1960's and early 1970's, battery operated drills were bulky, ill-balanced and required multiple batteries to perform some surgeries due to the limited energy storage capacity and poor efficiency of the electric motors.

Since then, manufacturers have attempted to make batteries more efficient with higher energy storage capacity, reduced size, and improved rechargeable lifespans. Likewise, motor housings such as saw and drill bodies have become more ergonomic, balanced, lightweight and energy efficient. As with may standard hand tools having multiple moving components, instrument manufacturers have reduced weight by utilizing lighter materials such as plastic housings, and gears, and put lightening holes in what were previously solid housings. In some cases, standard mountings for attachments have been replaced with modular fittings, allowing for greater interchangeability and component selections. Additionally, manufacturers have attempted to improve electrical components by upgrading them with more modern components wherever possible.

All of these improvements in equipment construction have improved efficiencies, costs and quality in some areas while at the same time increasing costs for acquisition, maintenance and increasing risks in other ways that were not previously seen or predicted. Often times cost and quality can be inversely proportional to one another. One example of the increased cost and reduced patient safety is seen in the cleaning and maintenance of instruments.

Recent published reports suggest that many of the surgical instruments used in operations were not being cleaned and/or sterilized appropriately in the very hospital facilities that were established and tasked for that purpose. In numerous reports, following cleaning and sterilization, it was noted that upon closer secondary inspection, the inside of small diameter cannulas and intricate mini-components of arthroscopic shavers that are used for many of today's minimally invasive procedures, contained human tissue and bone fragments from previous surgeries. In other cases, modular components of drills and saws such as chucks, drill bits and blades were found to have similar debris or pieces of cleaning brushes and/or bristles embedded in or on them. These investigations have demonstrated that in most cases the instruments were not cleaned according to manufacturer's specifications which has likely lead to many documented cases of serious, multiple, serial infections for subsequent patients. A pilot program conducted by the Centers for Medicare and Medicaid Services (Schaefer et al., 2010; JAMA 2010; 303(22):2273-2279) inspected 1500 outpatient surgery centers and found that 28% had been cited for infectious control deficiencies associated with equipment cleaning and sterilization. The costs to the patients and the hospitals in both expense and liability to deal with these infections can be and has been staggering.

In other cases, critical battery-operated, motorized tools such as drills or bone saws have ceased to function due to dead batteries that no longer maintain their capacity to hold a charge, or due to internal part failure, often attributable to overuse or lack of proper maintenance. The resultant downtime in the operating suite is extremely costly, as the procedure step must be put on hold while replacement or substitute tools are obtained. Wait times may often exceed 20-30 minutes, resulting in additional anesthesia exposure for the patient, additional operating room time (charged to the patient) and potential delays to other procedures where the replacement or substitute equipment had been scheduled for use in a later procedure. Recent estimates (2005) establish the average cost of operating room time to range between $62/min. (range $21.80-$133.12) depending on the procedure. These figures did not include extra resources provided by the hospital for special, non-routine situations which often occur during standard procedures, and did not include the surgeon and anesthesia provider fees, (anesthesia fees are estimated to be $4/min; range $2.20-$6.10). In each case, the hospital or surgical center must then take the equipment out of service, and send it back to the instrument manufacturer or other service provider for service or replacement.

Hospitals and instrument manufacturers are continuously attempting to find improved ways to reduce risk associated with infection in general, and more recently, specifically from improperly cleaned instruments. One approach has been to use more disposable, single-use instruments such as drills, saw blades and plastic cannulas. Additionally, many laparoscopic devices such as, surgical staplers and trocars, are designed as single use items that are intended to be immediately disposed of after use. Unfortunately, at today's acquisition costs, the total cost of ownership and benefits are not always clear for high-use battery-operated, motorized instruments such as saws, drills and reamers used in orthopedic procedures and the idea of disposable powered instruments has not been readily embraced.

A recent trend in the medical community is reprocessing of single use medical instruments, by parties other than the original equipment manufacturer, instead of discarding them after use. During reprocessing, the medical instruments are disassembled, cleaned and sterilized. They are then reassembled for future use. However, because the medical instruments reprocessed for further use are specifically provided for use during a single procedure, the performance of the medical instruments tend to decline after reprocessing because the components making up the medical instrument are not adapted for multiple uses and will degrade in performance when used beyond their intended life span. For example, reprocessing of the cutting devices on trocars is intended to extend these devices beyond their intended mission life, but often results in duller cutting edges on the blades because neither the materials used nor the reprocessing method can restore the device to the original manufacturing specifications. A greater force, therefore, is needed to make an initial incision, causing more trauma to the patient. In addition, the use of greater force increases the potential for error during the surgical procedure.

Most hospitals and surgery centers buy high-use, reusable motorized, pneumatic, wired or battery operated, orthopedic surgical equipment and are expected to clean, sterilize, and maintain them internally within the hospital. Unfortunately, the technicians hired to perform this work are typically not qualified or trained to perform this work adequately for the many varieties of powered instruments used. Further, manufacturers rarely provide the hospital/client with the training or diagnostic equipment necessary to evaluate or test the equipment. Often times the hospital employees responsible for cleaning and maintenance are not technicians at all, being paid slightly more than minimum wage, working at a fast pace to merely wash, count, and reload instruments into their appropriate system trays and flash sterilize them as quickly as possible, in an effort to keep the equipment in rotation in the hospital operating rooms, where higher throughput dictates profitability for the hospital or surgery center.

As a result of high throughput requirements, general maintenance is rarely done and preventative monitoring and maintenance is almost never done on this type of equipment. Hospital budgets for internal maintenance of equipment are generally geared toward high-end, multi-million-dollar capital equipment such as x-ray and radiological equipment. It is generally assumed that it is faster, simpler, and more economical for the hospital to wait for hand-held instruments, such as drills, saws and reamers to fail, then, send them back to the manufacturer for repair or replacement.

Thus it has become apparent that there is a need for an improved system of cost-effective, battery-operated, motorized tools in conjunction with better cleaning and maintenance protocols which can provide the hospital, surgeon, and most importantly, the patient, with a higher degree of efficiency and cleanliness while reducing risk and keeping the costs of cleaning, maintenance, and repair as low as possible.

SUMMARY

A surgical tool and attachment system includes a surgical power tool including a housing and a rotary powered driver. A power tool accessory unit includes a power tool accessory driver and an attachment member connected to the housing. A coupling interconnects the rotary powered driver and the power tool accessory unit.

DETAILED DESCRIPTION

Figure 1:
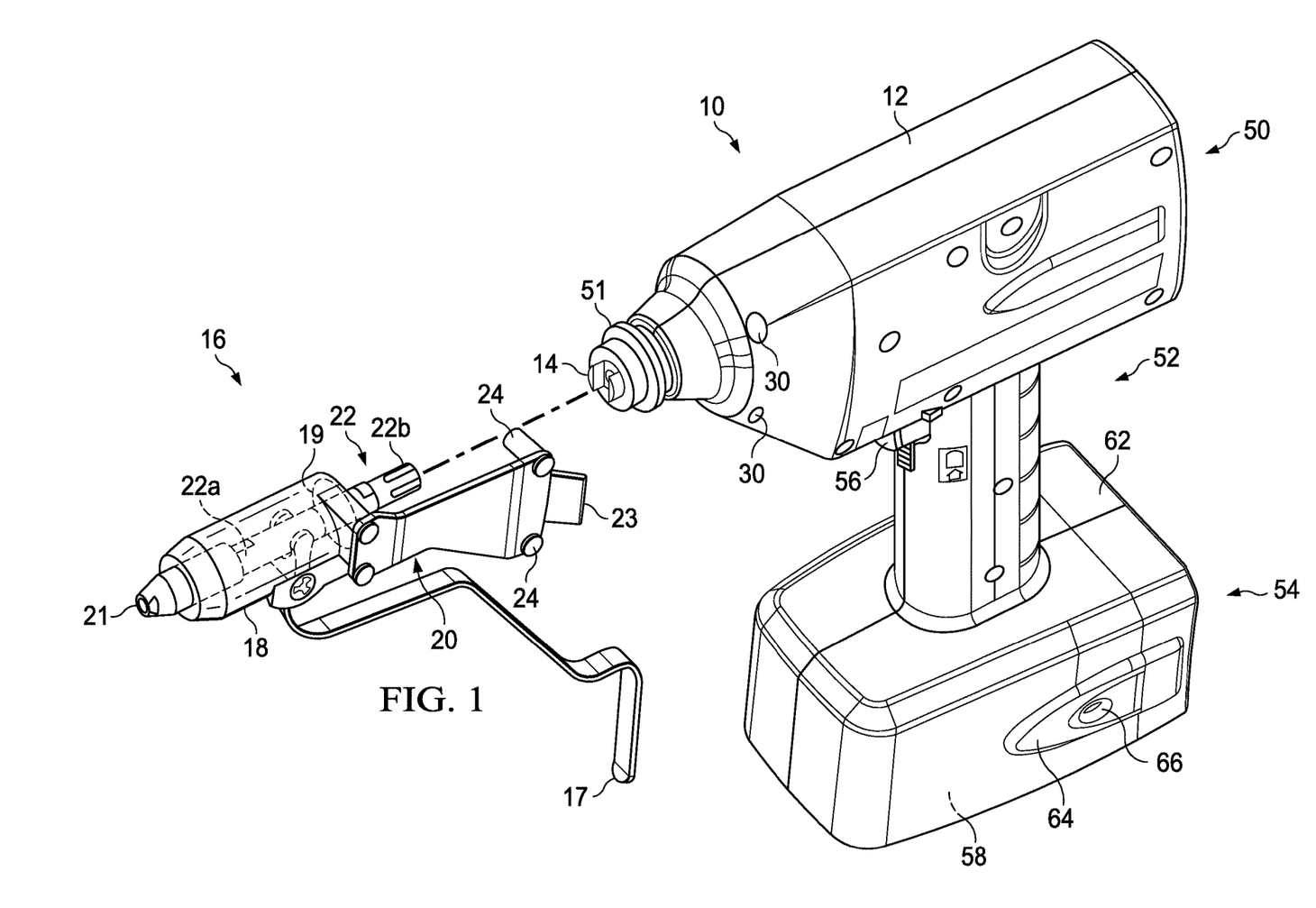
FIG. 1 is a perspective view illustrating an embodiment of a surgical power tool and an accessory unit attachable to the power tool.
Figure 2:
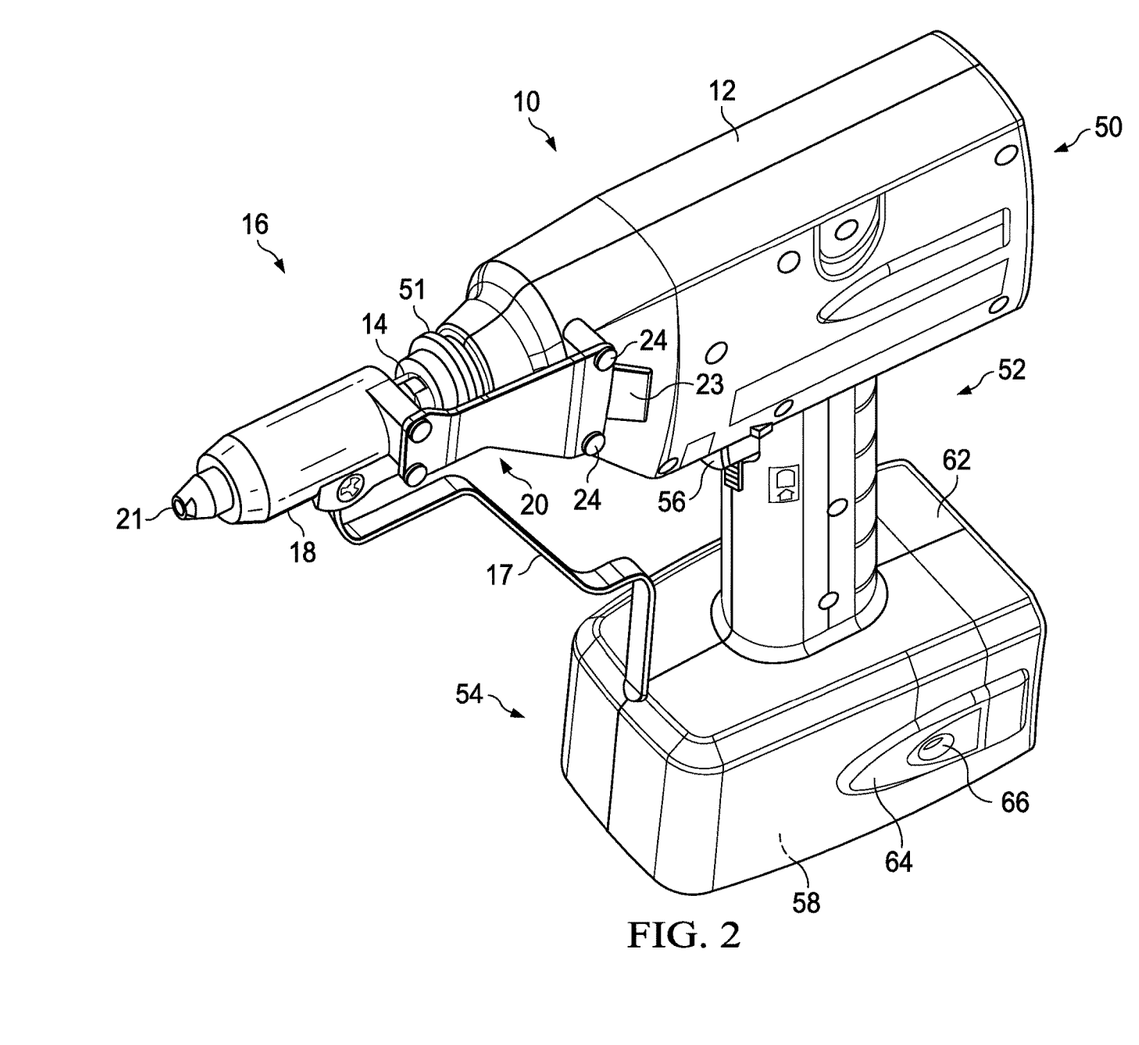
FIG. 2 is a perspective view of the surgical power tool of FIG. 1 attached to the accessory unit.

In one embodiment, FIGS. 1 and 2 illustrate a surgical tool attachment system comprising a surgical power tool 10 including an integrated housing 12 and a rotary powered driver 14. Also, a unitary power tool accessory unit 16 is illustrated and includes a power tool accessory driver 18, an attachment member 20 and an elongated coupling 22. The attachment member 20 is provided to be connected to the housing 12 as will be discussed below. Coupling 22, such as a modified Hudson quick connect is provided in unit 16 for interconnecting the rotary powered driver 14 and the power tool accessory driver 18. An elongated tubular shaped cavity 19 is provided in accessory driver 18 of accessory unit 16 for receiving the elongated coupling 22.

The unitary construction of the power tool accessory unit 16 includes three main components such as the power tool accessory driver 18, the attachment member 20 and coupling 22. The power tool accessory driver 18 is fixedly attached a flexible attachment member 20 including a tab 23. Also, power tool accessory unit 16 may include at least one protruding securing member 24 which is provided to be inserted into a mating receiver 30 in housing 12 adjacent to the rotary powered driver 14. A further component of power tool accessory unit 16 is a movable handgrip member 17 which can be connected to actuate the accessory driver 18 for driving wire or pins into human bone during a surgical procedure. A first end 22a of the coupling 22 is inserted into the accessory unit 16 and a second end 22b of the coupling 22 can be removably connected to the rotary power driver 14 when unit 16 is coupled to tool 10. In this manner, the coupling 22 can transfer rotary power directly to a rotary end 21 of the power tool accessory driver 18, in this instance, a wire driver. In FIGS. 1 and 2, the coupling 22 inserts directly into cavity 19 in the power tool accessory driver 18 of the power tool accessory unit 16. The tab 23 may be manually urged to flex the attachment member 20 when inserting and removing securing members 24 relative to receivers 30.

Figure 3:
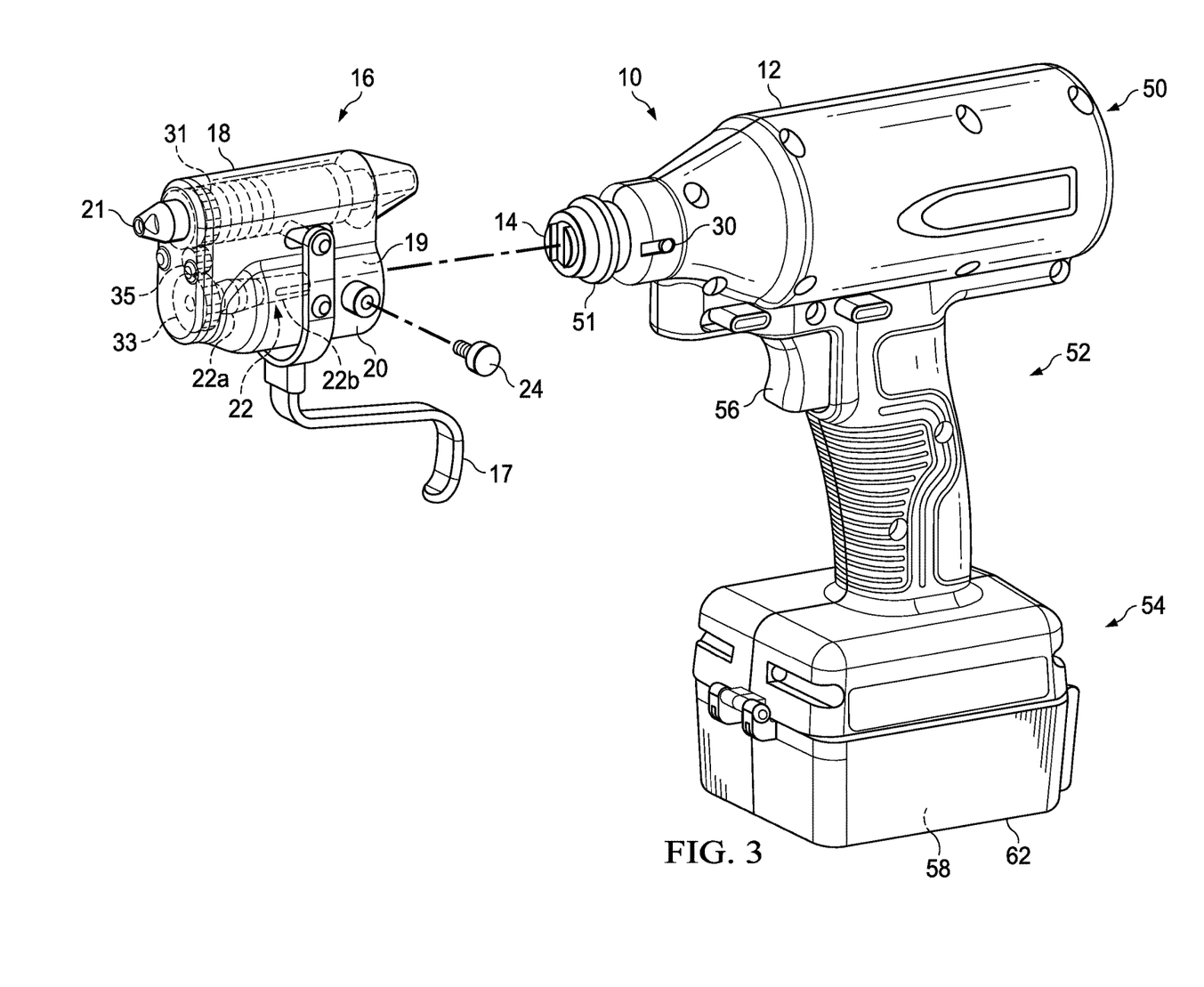
FIG. 3 is a perspective view illustrating another embodiment of a surgical power tool and an accessory unit attachable to the power tool.
Figure 4:
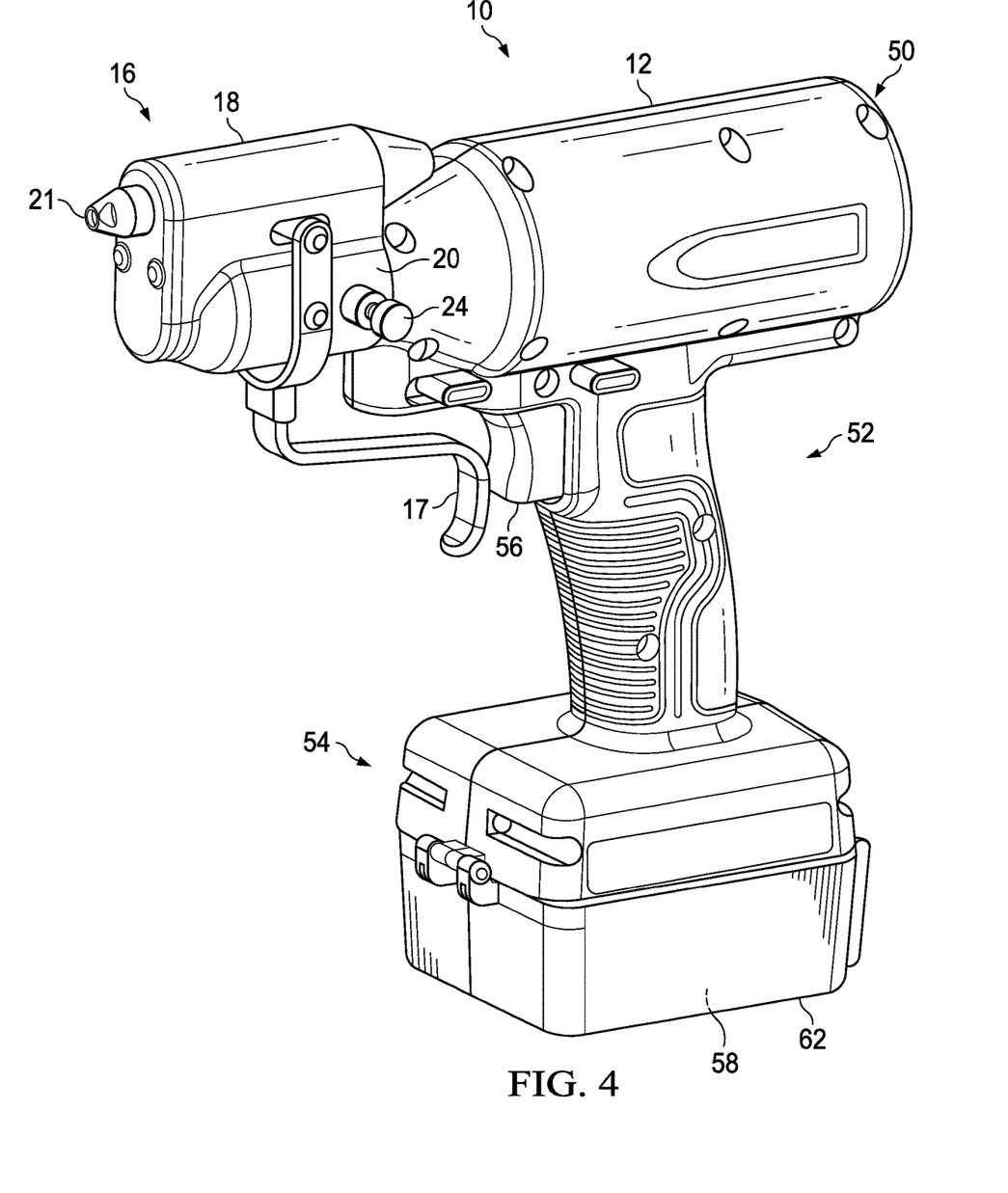
FIG. 4 is a perspective view and FIG. 5 is a side view of the surgical power tool of FIG. 3 attached to the accessory unit.
Figure 5:
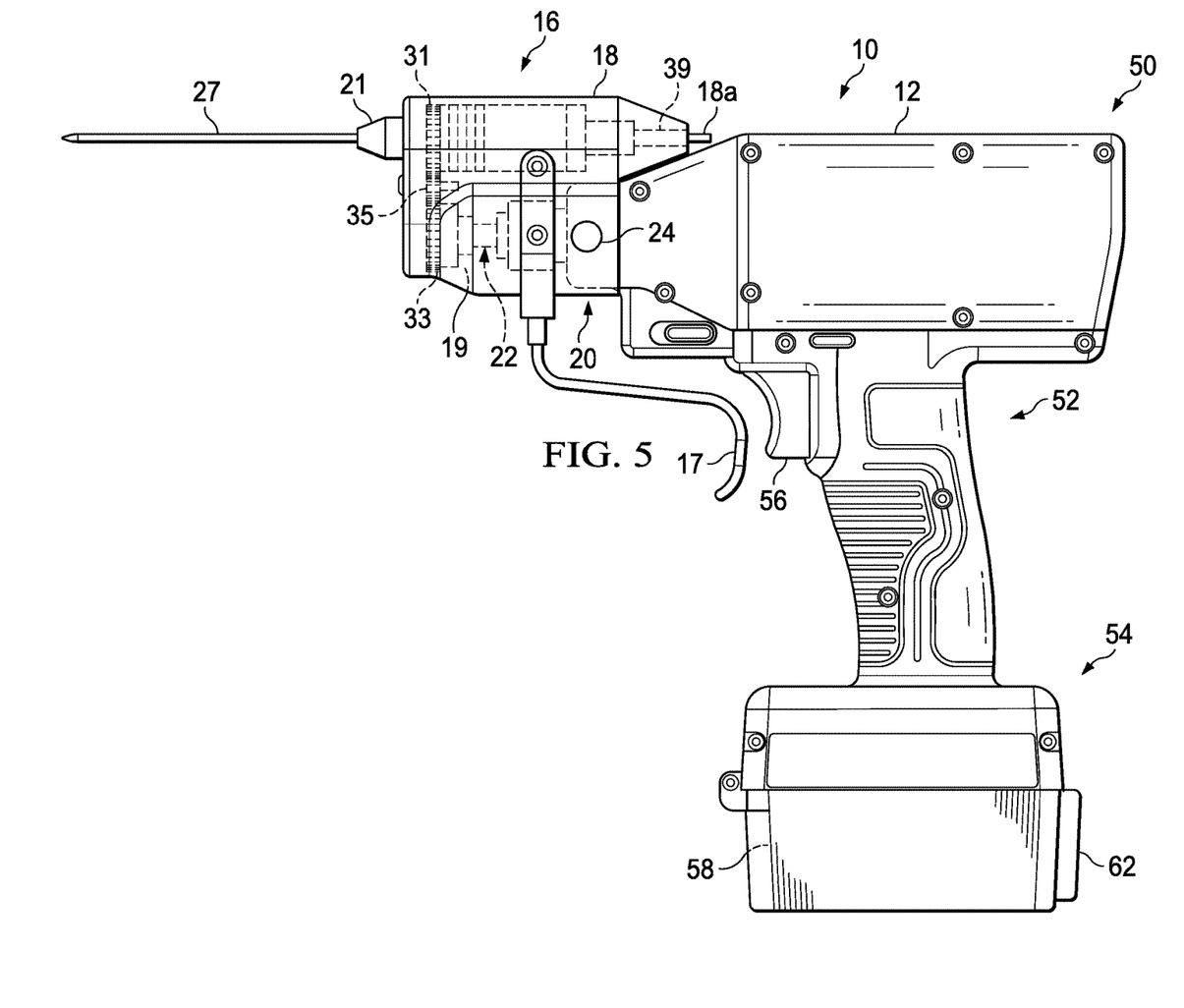
Figures 6, 7, 8:
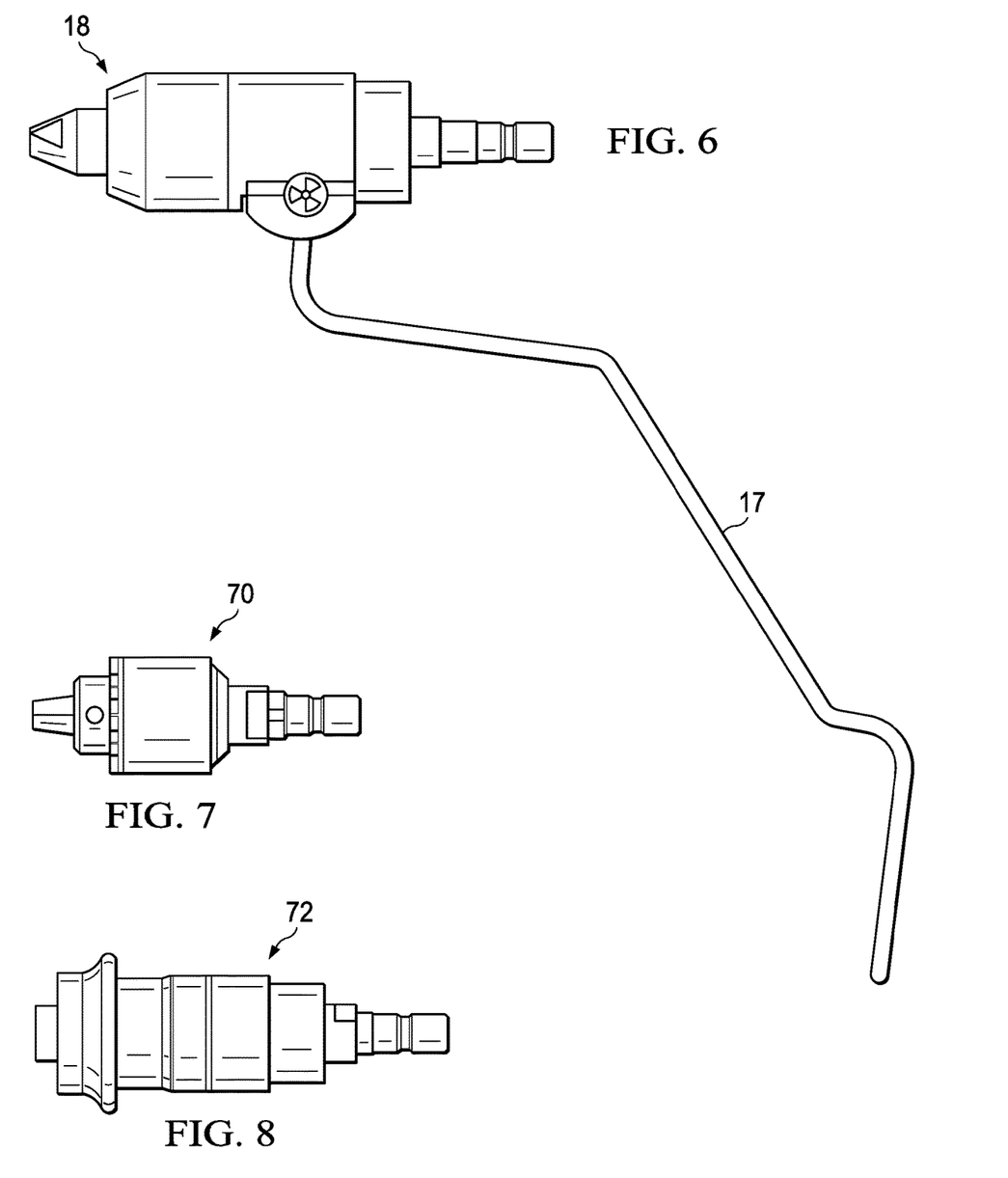
FIGS. 6-9 are side views illustrating embodiments of single-use accessories including a wire driver, a Jacob's chuck and a reamer speed reducer.

In another embodiment, FIGS. 3, 4 and 5 illustrate a surgical tool attachment system comprising a surgical power tool 10 including an integrated housing 12 and a rotary powered driver 14. Also, a unitary power tool accessory unit 16 is illustrated and includes a power tool accessory driver 18, an attachment member 20 and an elongated coupling 22. The attachment member 20 is provided to be connected to the housing 12 as will be discussed below. Coupling 22 is provided in unit 16 for interconnecting the rotary powered driver 14 and the power tool accessory driver 18. In the embodiments of FIGS. 1-5, corresponding parts are identified by the same reference numerals. In FIG. 5, the power tool 10 is illustrated with a piece of wire or pin 27 extending through a channel 39 of the accessory driver 18, from a rear portion 18a to the rotary end 21 of accessory driver 18, in this instance, a wire driver. The pin driver or wire driver 27 does not feed through the power tool 10 but, as shown, extends through accessory driver 18 externally of power tool 10. Extended handgrip/trigger member 17 can be actuated to grip or release the installed wire or pin 27, such as K-wire or Steinmann pins for use in orthopedic procedures. The unitary power tool accessory unit 16 includes the elongated power tool accessory driver 18 which extends longitudinally side-by-side with and parallel to the elongated attachment member 20. Thus, the gear 33, driven by the rotary powered driver 14 via coupling 22, drives the gear 31 via an idler gear 35 to transfer rotary power from coupling 22 to accessory driver 18. The gears 31, 33, 35 are illustrated as vertically stacked meshing gears, however the arrangement of the gears may be modified and achieve the same result.

The unitary construction of the power tool accessory unit 16 includes three main components such as the power tool accessory driver 18, the attachment member 20 and coupling 22. The power tool accessory driver 18 is fixedly attached to the attachment member 20. Also, power tool accessory unit 16 may include a threaded securing member 24 which is provided to be received by a mating threaded receiver 30 in housing 12 adjacent to the rotary powered driver 14. A further component of power tool accessory unit 16 is a movable handgrip member 17 which can be connected to actuate the accessory driver 18 for driving wire or pins into human bone during a surgical procedure. A first end 22a of the coupling 22 is inserted into the accessory unit 16 and a second end 22b of the coupling 22 can be removably connected to the rotary power driver 14 when unit 16 is coupled to tool 10. In this manner the coupling 22 can transfer rotary power to rotary end 21 of the power tool accessory driver 18, in this instance, a wire driver. In FIGS. 3-4, the coupling 22 inserts into cavity 19 of attachment member 20 adjacent the power tool accessory driver 18 of the power tool accessory unit 16. Elongated tubular shaped cavity 19 is provided adjacent accessory driver 18 within accessory unit 16 for receiving coupling 22. Gear set 31, 33, 35, transfers rotary motion from coupling 22 to accessory driver 18, see FIGS. 3 and 5.

The surgical power tool 10, of FIGS. 1-5 includes the integrated housing 12 having a power and attachment portion 50, a handle portion 52 and a battery housing portion 54. The power and attachment portion 50 contains an electric motor (not shown) and a chuck 51 for securing various accessories to the tool 10 as is known. The handle portion 52 includes a trigger 56, and the battery housing portion 54 defines a battery compartment 58 therein. The integrated housing 12 is preferably formed of a synthetic material and can comprise first and second half portions joined together. A battery (not shown) in battery compartment 58 may be either rechargeable or disposable. Battery housing 54 may include, as an example in some embodiments, a single unit molded door 62 having a pair of snap-on attachment members 64 and a pair of grip-to-remove members 66, only one being shown in the drawing FIGS. 1 and 2, or may include a hinged molded door 62, FIGS. 3-5.

It is also contemplated that significant savings can be realized in providing for single-use accessories, see FIG. 6-9, such as wire driver 18, a Jacob's chuck 70, and a reamer speed reducer 72, by manufacturing such accessories having at least 50% of the components made of low cost injection molded components formed of a suitable synthetic material and providing selected remaining components to be made of metal where critically needed.

Figure 9:
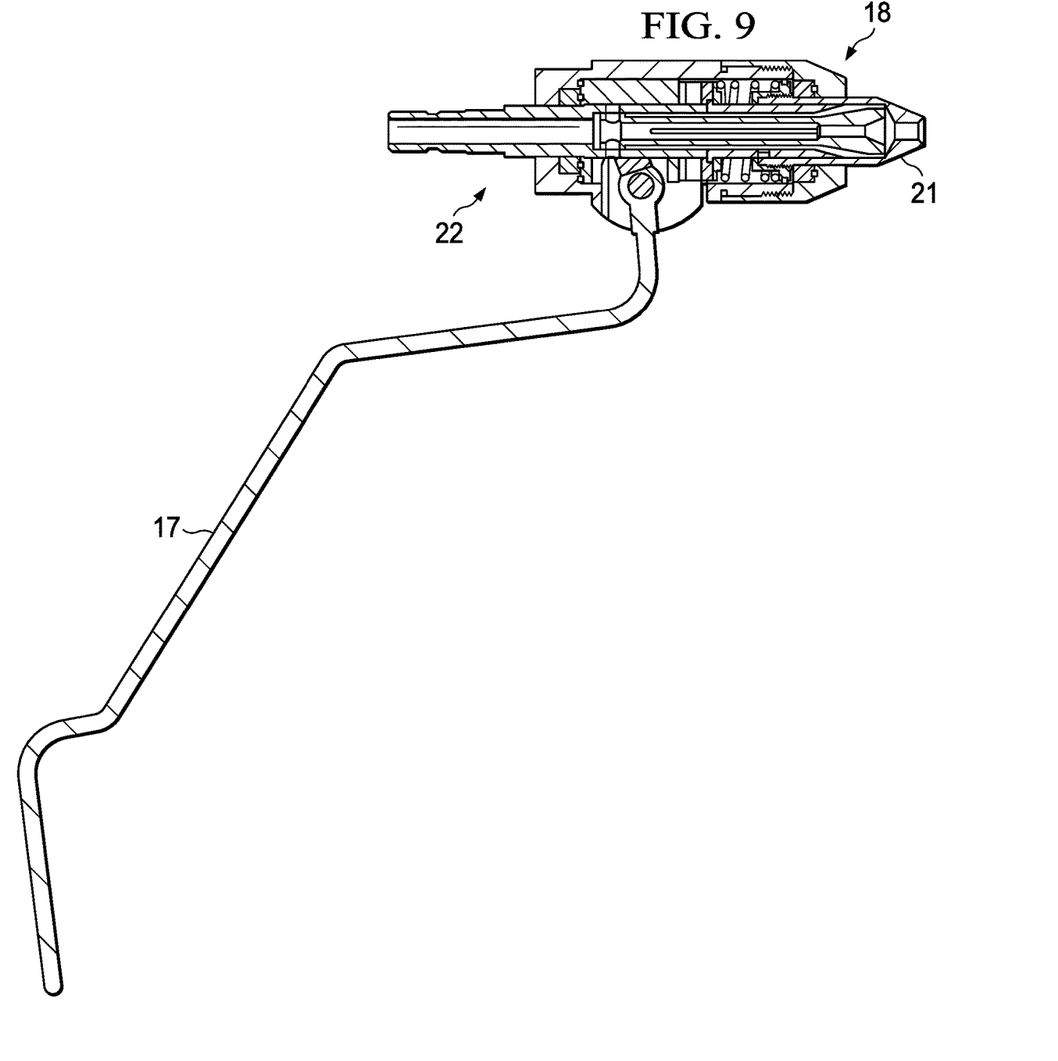

In FIG. 9, the wire driver 18 is illustrated in cross-section for the purpose of showing that a portion of the wire driver 18, up to 50%, can include components formed of a suitable synthetic material. In this example, the cross-hatch pattern is indicative of the metal portions of the wire driver 18, and also the handle 17, although the handle 17 can also be formed of a suitable synthetic material.

With the advent of single-use and limited use tools, utilizing a wire driver, chuck or the like that is traditionally high cost, machined stainless steel increases the cost and decreases the sterility advantages of a single or limited use tool. Utilizing a wire driver increases the cost of both the surgical tool and the wire driver. In order to attach a traditional wire driver to a tool, an expensive attachment scheme has been used which utilizes complex male and female interlocking components on the body of the rotary tool and also on the accessory. In order to maximize the benefits of a single or limited-use tool, a set of low cost, single or limited use accessories are needed. In order to reduce costs of both the tool and the wire driver, a lower cost attachment system is required.

A single-use or limited-use removable wire driver, composed primarily of plastic or other molded material can substantially reduce costs in comparison to the current iteration of the product which is primarily machined steel. The low-cost wire driver would be disposable after a single use or a limited number of uses, not expected to be greater than 20 procedures. A key element of the disclosure is low cost, injection molded outer components combined with a minimal use of more robust metallic parts where necessary to maintain functional usefulness over the limited life of the device. This disclosure lowers the cost-per-procedure and minimizes sterility risks in comparison to utilizing traditional machined steel equivalents, especially when using the accessory in a single-use, disposable application.

A single-use or limited-use chuck is composed primarily of plastic or other molded material will substantially reduce costs in comparison to the current iteration of the product which is primarily machined steel. The low cost, removable chuck would be disposable after a single use or a limited number of uses, not expected to be greater than 20 procedures. A key element of the device and system is low cost, injection molded outer components combined with a minimal use of more robust metallic parts where necessary to maintain functional usefulness over the limited life of the device. This device and system lowers the cost-per-procedure and minimizes sterility risks in comparison to utilizing traditional machined steel equivalents, especially when using the attachment in a single-use, disposable application.

A single-use or limited-use Reamer Speed Reducer, which has a primary function to reduce RPM and increase torque of the rotating instrument, for powered surgical tools is composed primarily of plastic or other molded material to substantially reduce costs in comparison to the current iteration of the product which is primarily machined steel. The low cost, removable accessory would be disposable after a single use or a limited number of uses, not expected to be greater than 20 procedures. A key element of the device and system is low cost, injection molded outer components combined with a minimal use of more robust metallic parts where necessary to maintain functional usefulness over the limited life of the device. This device and system lowers the cost-per-procedure and minimizes sterility risks in comparison to utilizing traditional machined steel equivalents, especially when using the attachment in a single-use, disposable application.

A single-use or limited-use adapter, reamer shaft or other accessory for powered surgical tools are composed primarily of plastic or other molded material to substantially reduce costs in comparison to the current iteration of the product which is primarily machined steel. The low cost, removable adapter, reamer shaft or other accessory would be disposable after a single use or a limited number of uses, not expected to be greater than 20 procedures. A key element of the device is low cost, injection molded outer components combined with a minimal use of more robust metallic parts where necessary to maintain functional usefulness over the limited life of the device. This device and system lowers the cost-per-procedure and minimizes sterility risks in comparison to utilizing traditional machined steel equivalents, especially when using the accessory in a single-use, disposable application.

The device and system utilizes a simple, low cost attachment system for a wire driver and other accessories commonly used with powered surgical instruments. Surgical power tools and associated accessories currently utilize the complex attachment scheme mentioned above, which is a holding device, specifically, a subtype of chuck that forms a collar around the object to be held and exerts a strong clamping force on the object when it is tightened, usually by means of a tapered outer collar. This system requires multiple, expensive components that drive up the cost of the power tool as well as the attachment. The device removes the necessity of the complex attachment scheme for certain accessories such as a wire driver, removing cost from both the power tool and the accessory.

The device and system uses a male/female coupling on the wire driver and power tool to attach the rotating mechanism, combined with an adapter plate with locating pins which eliminates any clockwise or counterclockwise rotation of the wire driver when the surgical drill shaft is rotating. The adapter plate can be modified to attach to the right, left or both sides of the tool, as well as modifying pin locations depending on the tool housing structure.

Although illustrative embodiments have been shown and described, a wide range of modification, change and substitution is contemplated in the foregoing disclosure and in some instances, some features of the embodiments may be employed without a corresponding use of other features. Accordingly, it is appropriate that the appended claims be construed broadly and in a manner consistent with the scope of the embodiments disclosed herein.

What is claimed is:

1. A surgical tool attachment system comprising:
   a single use or limited-use, battery-operated surgical power tool including a housing formed of a synthetic material comprising a first portion and a second portion joined together, said housing having an integrated rotary powered driver; and
   a power tool accessory unit including an elongated tubular-shaped interior cavity, a power tool accessory driver, attachment member configured for external attachment of the power tool accessory unit to the housing, and an elongated coupling interconnecting the power tool accessory driver and the rotary powered driver,
   wherein said attachment member comprises either a flexible portion or a collar configured to removably attach the power tool accessory unit to the external housing adjacent to the rotary powered driver.

2. The system of claim 1 further comprising:
   at least one securing member connected to the attachment member and configured for external attachment to a mating receiver in the housing.

3. The system of claim 2, wherein
   the at least one securing member comprises a protruding pin or a threaded securing member and is connected to the mating receiver in the external housing.

4. The system of claim 3, wherein the mating receiver is adjacent the rotary powered driver.

5. The system of claim 1, further comprising:
   a movable handgrip member connected to the power tool accessory driver to both actuate the accessory driver and to grip or release a wire or pin.

6. The system of claim 1, wherein a first end of the elongated coupling is insert into the elongated tubular-shaped cavity of the accessory unit and a second end of the coupling is removably connected to the rotary power driver.

7. The system of claim 1, wherein the attachment member includes a tab extending from the flexible portion.

8. The system of claim 7, wherein the tab may be manually urged to flex the attachment member when inserting and removing the at least one securing member relative to the receiver in the external housing adjacent the rotary powered driver.

9. The system of claim 1, the surgical power tool further consisting of:
   an extended handgrip and trigger member;
   a battery housing portion comprising a battery compartment therein; and
   a battery in the battery compartment;
   wherein said battery is either rechargeable or disposable.

10. The system of claim 1 wherein the attachment member includes the elongated tubular-shaped interior cavity comprising the elongated coupling coaxially positioned within the power tool accessory driver.

11. The system of claim 1 wherein the attachment member includes the elongated tubular-shaped interior cavity comprising the elongated coupling adjacent to and offset from the power tool accessory driver, wherein two drive gears and an idler gear transfer rotary motion from the elongated coupling to the accessory driver.

12. The system of claim 11 wherein the securing member includes a threaded member mounted in the attachment member and engaged with a mating threaded receiver in the external housing adjacent the rotary powered driver.

13. A low-cost surgical tool and attachment system comprising:
   a limited-use, battery-operated surgical power tool including a housing having an integral rotary powered driver, the housing being an integrated housing formed of a synthetic material comprising a first portion and a second portion joined together, said integrated housing having a power portion comprising the rotary powered driver comprising an electric motor, a handle portion with a trigger and an accessible battery housing portion comprising either a rechargeable or disposable battery; and
   a single-use or limited-use power tool accessory unit comprising plastic and injection molded components to reduce cost including an elongated tubular-shaped interior cavity, a power tool accessory driver;
   flexible attachment member configured for external attachment of the power tool accessory unit to the housing; and
   an elongated coupling interconnecting the power tool accessory driver and the rotary powered driver,
   wherein said power tool accessory unit would be disposable after a single use or a limited number of uses, not expected to be greater than 20 procedures, and
   wherein said attachment member is configured to removably attach the power tool accessory unit to the external housing.

14. The system of claim 13, further comprising:
at least one, securing member connected to the flexible attachment member and configured for external attachment to a mating receiver in the housing.

15. The system of claim 14, further comprising:
the at least one securing member comprises a protruding pin or a threaded securing member and is connected to the mating receiver in the external housing.

16. The system of claim 15, wherein the mating receiver is adjacent the rotary powered driver.

17. The system of claim 13, further comprising:
a moveable handgrip member connected to the accessory driver to both actuate the accessory driver and to grip or release a wire or pin.

18. The system of claim 13, wherein a first end of the elongated coupling inserted into the elongated tubular-shaped cavity of the accessory unit and a second end of the elongated coupling is removably connected to the rotary powered driver.

19. The system of claim 13 wherein a pin/wire extends through a channel in the accessory driver externally of the power tool.

20. The system of claim 13 wherein the power tool accessory driver extends longitudinally side-by-side with and parallel to the attachment member.

21. The system of claim 20 further comprising:
a plurality of vertically stacked meshing gears driven by the rotary powered driver via the coupling, whereby rotary power is directly transferred from the coupling to the offset axis of the side-by-side and parallel accessory driver.

* * * * *